United States Patent [19]
Gaa et al.

[11] Patent Number: 5,594,142
[45] Date of Patent: Jan. 14, 1997

[54] PROCESS FOR THE PREPARATION OF POLYALKYL-1-OXA-DIAZASPIRODECANE COMPOUNDS

[75] Inventors: Karl Gaa, Burtenbach; Günter Nowy, Aystetten; Georg Schmailzl, Neusäss, all of Germany

[73] Assignee: Hoechst Aktiengesellschaft, Frankfurt am Main, Germany

[21] Appl. No.: 389,310

[22] Filed: Feb. 16, 1995

[30] Foreign Application Priority Data

Feb. 19, 1994 [DE] Germany ............... 44 05 387.8

[51] Int. Cl.$^6$ .................................. C07D 498/10
[52] U.S. Cl. .................. 546/19; 548/225; 528/367
[58] Field of Search ............... 546/19; 548/225; 528/367

[56] References Cited

U.S. PATENT DOCUMENTS 4,771,091  9/1988  Ertl ............................................. 524/97
5,169,925  12/1992  Schmailzl et al. ...................... 528/367

FOREIGN PATENT DOCUMENTS 0224181  6/1987  European Pat. Off. .
0402889  12/1990  European Pat. Off. .
0575776  12/1993  European Pat. Off. .

OTHER PUBLICATIONS

March, J. *Advanced Organic Chemistry* (John Wiley, New York), p. 391 (1992).
Pascal, J. et al. *J. Med. Chem.* 28, 647–652 (1985).
Bernauer, K. et al. *Helvetica Chimica Acta* 76, 2263–2273 (Oct. 1993).

*Primary Examiner*—Mukund J. Shah
*Assistant Examiner*—King Lit Wong
*Attorney, Agent, or Firm*—Connolly and Hutz

[57] ABSTRACT

The invention relates to a process for the preparation of polyalkyl-1-oxa-diazaspirodecane compounds, which can be used as highly active light stabilizers for polymers. The reaction is carried out in a solvent mixture of at least one alcohol and if appropriate an inert organic solvent in the presence of solid alkali metal hydroxide or a corresponding amount of a mixture of solid alkali metal hydroxide and water as the sole catalyst. The process offers the advantage that, by using a solvent mixture and dispensing with a phase transfer catalyst, a higher rate of reaction and therefore higher product quality with the same yield are achieved. By dispensing with a phase transfer catalyst, which remains in the waste water and must be disposed of expensively, and by the reusability of the solvent mixture, the process is more environment-friendly and more economical than processes known to date.

8 Claims, No Drawings

PROCESS FOR THE PREPARATION OF POLYALKYL-1-OXA-DIAZASPIRODECANE COMPOUNDS

The invention relates to a process for the preparation of polyalkyl-1-oxa-diazaspirodecane compounds which can be used as highly active light stabilizers for polymers.

Compounds of the formula

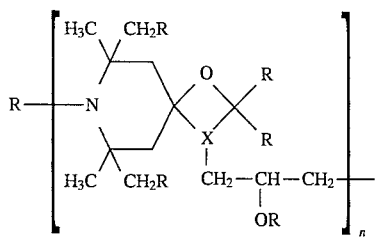

are known (cf. EP 402 889). The preparation process for these compounds comprises carrying out the synthesis in an inert solvent in the presence of solid or aqueous alkali metal hydroxides and in addition a phase transfer catalyst. However, the addition of a phase transfer catalyst has the disadvantage that it enters the waste water during working up of the reaction mixture and thus causes environmental pollution. In particular, the quaternary ammonium or phosphonium halides, which are described as particularly active, render the discharge of the waste water into a biological clarification plant impossible, since quaternary ammonium and phosphonium salts have a bactericidal action and cannot be worked up in a biological clarification plant. The waste water must therefore be disposed of expensively as special waste.

There was thus the object of discovering a process which renders the compounds mentioned possible within the shortest possible reaction times and in the highest possible yields with at least the same product quality, without at the same time having the disadvantages known from the prior art of inadequate environment-friendliness and the resulting expensive disposal of waste water.

It has been found that the object can be achieved if solid or aqueous alkali metal hydroxide is used as the sole catalyst for the preparation of the compounds mentioned and the reaction is carried out in a solvent mixture comprising at least one alcohol and if appropriate an inert solvent, which can advantageously be recovered.

The present invention thus relates to a process for the preparation of polyalkyl-1-oxa-diazaspirodecane compounds of the formula I

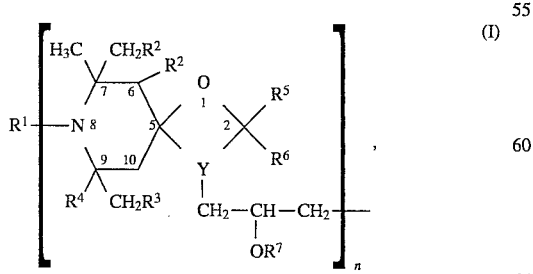

in which
n is an integer from 1 to 50 and

Y is a group of the formula II or III

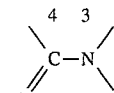 (II)

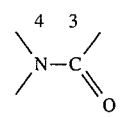 (III)

in which the indices 3 and 4 indicate the ring positions in the diazaspirodecane system and one bond of the nitrogen is linked to a $CH_2$ group of the propylene-2-oxy group, $R^1$ is a hydrogen atom, an oxygen atom, an NO group, a $C_1$–$C_{12}$-alkyl group, an allyl group, a $C_1$–$C_{22}$-acyl group, a benzyl group, a $C_1$–$C_{12}$-alkyloxy group or a $C_3$–$C_{12}$-cycloalkoxy group, $R^2$ and $R^3$ are either identical and are a hydrogen atom or a $C_1$–$C_5$-alkyl, in which case $R^4$ is a methyl group, or $R^2$ is a hydrogen atom or a $C_1$–$C_5$-alkyl group and $R^3$ and, $R^4$, together with the carbon atoms joining them, form a $C_5$- or $C_6$-cycloalkyl group or a group of the formula

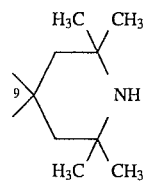

$R^5$ and $R^6$ are identical or different and represent a hydrogen atom, a $C_1$–$C_{30}$-alkyl group or a $C_7$–$C_{12}$-phenyl-alkyl group which is unsubstituted or substituted by chlorine or $C_1$–$C_4$-alkyl, or $R^5$ and $R^6$, together with the carbon atom joining them, form a $C_5$–$C_{18}$-cycloalkyl group which is unsubstituted or substituted by up to four $C_1$–$C_4$-alkyl groups, or a group of the formula

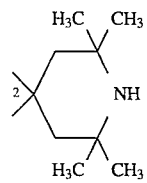

$R^7$ if n=1, has no meaning, so that the oxygen atom is bonded to the terminal $CH_2$ group and forms an oxirane ring, or $R^7$, if n>1, is a hydrogen atom or a $C_1$–$C_{22}$-acyl group or has no meaning in the terminal monomer unit, so that the oxygen atom is bonded to the terminal $CH_2$ group and forms an oxirane ring, by reaction of a compound of the formula IV

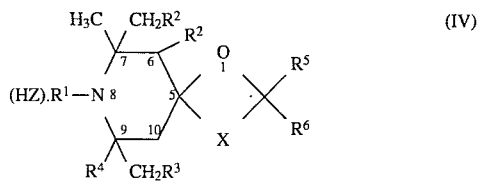 (IV)

in which $R^1$, $R^2$, $R^3$, $R^4$, $R^5$ and $R^6$ have the abovementioned meaning and (HZ) is an acid radical, or a salt thereof with a proton acid, with an epihalohydrin of the formula V

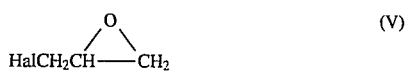

in which Hal is a chlorine, bromine or iodine atom, in a molar ratio of 1:1 to 1:10 in the presence of an alkali metal hydroxide in an organic solvent, and, if n>1, heating the resulting epoxy compound VI

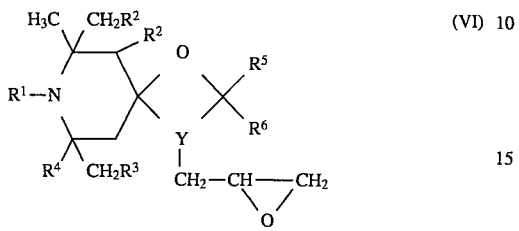

in which $R^1$, $R^2$, $R^3$, $R^4$, $R^5$ and $R^6$ have the abovementioned meaning, to a temperature of 100° to 240° C., which comprises carrying out the reaction of the compound of the formula IV with the compound of the formula V in the presence of the equimolar to twenty times the molar amount of solid alkali metal hydroxide or of the corresponding amount of a mixture of solid alkali metal hydroxide and water in a weight ratio of 1:9 to 9:1 as the sole catalyst in a solvent mixture of at least one alcohol and if appropriate an inert organic solvent.

In the formula (I) of the polyalkyl-1-oxa-diazaspirodecane compounds

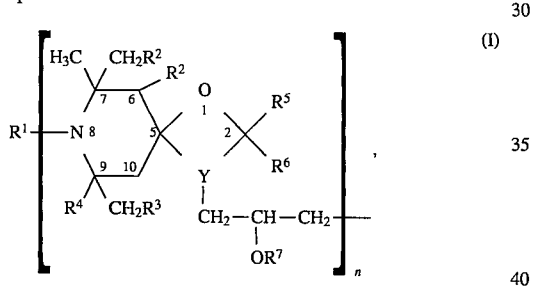

to be prepared according to the invention, n is an integer from 1 to 50, preferably 1 to 15, in particular 1 to 7.

Y is a group of the formula II or III

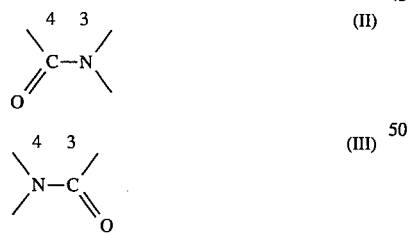

in which the indices 3 and 4 indicate the ring positions in the diazaspirodecane system and one bond of the nitrogen is linked to a $CH_2$ group of the propylene-2-oxy group.

$R^1$ is a hydrogen atom, an oxygen atom, an NO group, a $C_1$–$C_{12}$-, preferably $C_1$–$C_4$-alkyl group, an allyl group, a $C_1$—$C_{22}$-acyl group, preferably an acetyl group, a benzyl group, a $C_1$–$C_{12}$-, preferably $C_1$–$C_4$-alkyloxy group or a $C_3$–$C_{12}$-, preferably $C_3$–$C_6$-cycloalkoxy group.

$R^2$ and $R^3$ are either identical or different and are a hydrogen atom or a $C_1$–$C_5$-alkyl group, preferably a hydrogen atom, in which case $R^4$ is a methyl group, or $R^2$ is a hydrogen atom or a $C_1$–$C_5$-alkyl group and $R^3$ and $R^4$, together with the carbon atoms joining them, form a $C_5$- or $C_6$-cycloalkyl group or a group of the formula

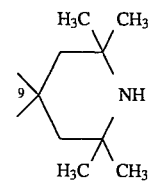

$R^5$ and $R^6$ are identical or different and are a hydrogen atom, a $C_1$–$C_{30}$-, preferably $C_1$–$C_{18}$-alkyl group or a $C_7$–$C_{12}$-phenylalkyl group which is unsubstituted or substituted by chlorine or $C_1$–$C_4$-alkyl, or $R^5$ and $R^6$, together with the carbon atom Joining them, form a $C_5$–$C_{18}$-cycloalkyl group which is unsubstituted or substituted by up to four $C_1$–$C_4$-alkyl groups, or a group of the formula

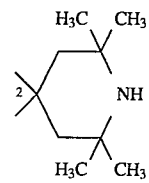

If n=1, $R^7$ has no meaning, so that the oxygen atom is bonded to the terminal $CH_2$ group and forms an oxirane ring.

If n>1, $R^7$ is a hydrogen atom or a $C_1$–$C_{22}$-, preferably $C_1$–$C_{12}$-acyl group, or has no meaning in the terminal monomer unit, so that the oxygen atom is bonded to the terminal $CH_2$ group and forms an oxirane ring.

The compounds of the formula (I) are prepared in accordance with the following reaction equation:

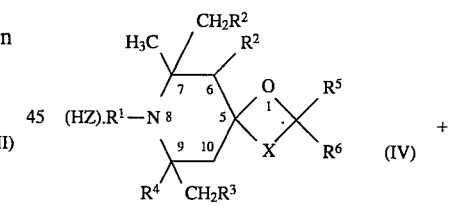

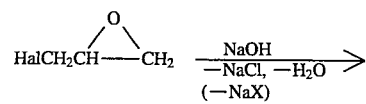

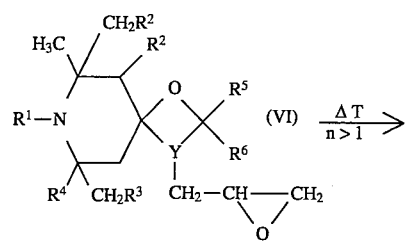

-continued

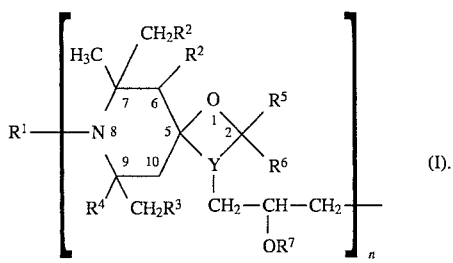

In the formulae of the reaction equation, the radicals R², R³, R⁴, R⁵, R⁶, Y, Hal and n have the abovementioned meanings: the radical R¹ is hydrogen and the radical R⁷ is also hydrogen or has no meaning in the terminal monomer unit, so that the oxygen atom forms an oxirane ring with the terminal CH₂ group.

Suitable compounds of the formula IV are, for example,
2-iso-propyl-7,7,9,9-tetramethyl-1-oxa-3,8-diaza-4-oxo-spiro-[4,5]-decane,
2-butyl-7,7,9,9-tetramethyl-1-oxa-3,8-diaza-4-oxo-spiro[4,5]-decane,
2-iso-butyl-7,7,9,9-tetramethyl-1-oxa-3,8-diaza-4-oxo-spiro-[4,5]-decane,
2-pentyl-7,7,9,9-tetramethyl-1-oxa-3,8-diaza-4-oxo-spiro [4,5]-decane,
2-hexyl-7,7,9,9-tetramethyl-1-oxa-3,8-diaza-4-oxo-spiro[4,5]-decane,
2-heptyl-7,7,9,9-tetramethyl-1-oxa-3,8-diaza-4-oxo-spiro [4,5]-decane,
2-iso-heptyl-7,7,9,9-tetramethyl-1-oxa-3,8-diaza-4-oxo-spiro-[4,5]-decane,
2-iso-octyl-7,7,9,9-tetramethyl-1-oxa-3,8-diaza-4-oxo-spiro-[4,5]-decane,
2-nonyl-7,7,9,9-tetramethyl-1-oxa-3,8-diaza-4-oxo-spiro[4,5]-decane,
2-iso-nonyl-7,7,9,9-tetramethyl-1-oxa-3,8-diaza-4-oxo-spiro-[4,5]-decane,
2-undecyl-7,7,9,9-tetramethyl-1-oxa-3,8-diaza-4-oxo-spiro-[4,5]-decane,
2-phenyl-7,7,9,9-tetramethyl-1-oxa-3,8-diaza-4-oxo-spiro [4,5]-decane,
2-(4-chloro-phenyl)-7,7,9,9-tetramethyl-1-oxa-3,8-diaza4-oxo-spiro-[4,5]-decane,
2,2-dimethyl-7,7,9,9-tetramethyl-1-oxa-3,8-diaza-4-oxo-spiro-[4,5]-decane,
2-ethyl-2,7,7,9,9-pentamethyl-1-oxa-3,8-diaza-4-oxo-spiro-[4,5]-decane,
2-propyl-2,7,7,9,9-pentamethyl-1-oxa-3,8-diaza-4-oxo-spiro-[4,5]-decane,
2-iso-propyl-6,7,7,9,9-pentamethyl-1-oxa-3,8-diaza-4-oxo-spiro-[4,5]-alecane,
2-butyl-2,7,7,9,9-pentamethyl-1-oxa-3,8-diaza-4-oxo-spiro-[4,5]-decane,
2-iso-butyl-2,7,7,9,9-pentamethyl-1-oxa-3,8-diaza-4-oxo-spiro- [4,5]-alecane,
2-pentyl-6,7,7,9,9-pentamethyl-1-oxa-3,8-diaza-4-oxo-spiro-[4,5]-alecane,
2-hexyl-2,7,7,9,9-pentamethyl-1-oxa-3,8-diaza-4-oxo-spiro-[4,5]-alecane,
2-nonyl-2,7,7,9,9-pentamethyl-1-oxa-3,8-diaza-4-oxo-spiro-[4,5]-decane,
2,2-diethyl-7,7,9,9-tetramethyl-1-oxa-3,8-diaza-4-oxo-spiro-[4,5]-alecane,
2,2-dipropyl-7,7,9,9-tetramethyl-1-oxa-3,8-diaza-4-oxo-spiro-[4,5]-alecane,
2,2-dibutyl -7,7,9,9-tetramethyl-1-oxa-3,8-diaza-4-oxo-spiro-[4,5]-alecane,
2-ethyl-2-pentyl-7,7,9,9-tetramethyl-1-oxa-3,8-diaza-4-oxo-spiro-[4,5]-alecane,
2,2-dibenzyl-7,7,9,9 -tetramethyl-1-oxa-3,8-diaza-4-oxo-spiro-[4,5]-alecane,
2,2,4,4-tetramethyl-7-oxa-3,12-diaza-14-oxo-dispiro[5,1,4,2]-tetradecane,
2,2,4,4-tetramethyl-7-oxa-3,20-diaza-21-oxo-dispiro[5,1,11,2]-heneicosane,
2,2,4,4-tetramethyl-7-oxa-3,14-diaza-15-oxo-dispiro[5,5,5,2]-pentadecane,
2,2,4,4,10,10,12,12-octamethyl-7-oxa-3,11,14-triaza-15-oxo-dispiro-[5,1,5,2]-pentadecane,
2-ethyl -2,7,7,9,9-pentamethyl-1-oxa-3,8-diaza-4-oxo-8-oxyl-spiro-[4,5]-alecane.

The polyalkyloxadiazaspirodecanes used as starting substances are known and are accessible in accordance with the instructions given in U.S. Pat. No. 4,110,334 and U.S. Pat. No. 4,107,139.

2,2,4,4 -Tetramethyl-7-oxa-3,20-diaza-21-oxo-dispiro[5,1,11,2]-heneicosane or the hydrochloride thereof is particularly preferred among the compounds IV.

The compound of the formula IV is reacted with an epihalohydrin of the formula V, in which Hal is to be understood as meaning a chlorine, bromine or iodine atom, preferably chlorine, in a molar ratio of 1:1 to 1:10, preferably 1:1 to 1:5 and in particular 1:1 to 1:3. The reaction is carried out in a solvent mixture comprising at least one alcohol and if appropriate an inert organic solvent in the presence of the equimolar to twenty times the molar amount of solid alkali metal hydroxide or of the corresponding amount of a mixture of solid alkali metal hydroxide and water in a weight ratio of 1:9 to 9:1, preferably 4:6 to 8:2, and in particular 5:5 to 7:3.

The reaction temperature is in the range from 20° to 220° C., preferably 40° to 120° C., and in particular 60° to 100° C.

The reaction mixture comprises at least one alcohol as the organic solvent. A straight-chain or branched alcohol having a chain length of $C_1$ to $C_{10}$, preferably $C_1$ to $C_4$, and in particular isopropanol, is suitable as the alcohol. The alcohol is employed in an amount of 1 to 100, preferably 20 to 80, in particular 30 to 70% by weight, based on the total amount of solvent.

In addition to the alcohol, the reaction mixture comprises an inert organic solvent. A suitable solvent is an aliphatic or atomatic hydrocarbon, such as, for example, petroleum ether, hexane, heptane, petroleum fractions, toluene, cyclohexane, xylene and the like.

The reaction has in general ended after 30 to 60 minutes.

After the reaction, the reaction mixture is concentrated until the alcohol and the excess epihalohydrin have distilled off completely and are thus recovered at the same time.

Thereafter, fresh inert solvent and water are added to the reaction mixture. The phases are separated, the organic phase is washed several times with water and the solvent is distilled off, the product being dried azeo-tropically at the same time.

The epoxide VI, which is usually obtained as an oil, can be isolated (n=1) or converted into a solid, amorphous polymer I, which is initially obtained in vitreous form, where n>1 by heating to 100° to 240° C., preferably 120° to 220° C., and in particular 150° to 200° C., without further purification. Low degrees of polymerization can be achieved by a short polymerization duration and high degrees of polymerization by a long duration of polymerization. Furthermore, there is a tendency towards higher degrees of polymerization as the temperature increases over the same duration of polymerization. For products obtained under the same polymerization conditions, the solution viscosity depends on the degree of reaction of compound IV with the epihalohydrin V and is thus a measure of the purity of the epoxide VI before the polymerization.

After the polymerization, the polymer can—if desired—be derivatized by methods known per se on positions $R^1$ and $R^7$ of the molecule.

The compounds prepared by the process according to the invention are used as light stabilizers in organic polymers, for example in those listed below:

1. Polymers of mono-and diolefins, for example polyethylene of high, medium or low density (which can be crosslinked if appropriate), polypropylene, polyisobutylene, polybut-1-ene, polymethylpent-1-ene, polyisoprene or polybutadiene, and polymers of cycloolefins, such as, for example, of cyclopentene or norbornene.
2. Mixtures of the polymers mentioned under 1), for example mixtures of polypropylene with polyethylene or with polyisobutylene.
3. Copolymers of mono-and diolefins with one another or with other vinyl monomers, such as, for example, ethylene-propylene copolymers, propylene-but-1-ene copolymers, propylene-isobutylene copolymers, ethylene-but-1-ene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and salts thereof (ionomers), as well as terpolymers of ethylene with propylene and a diene, such as hexadiene, dicyclopentadiene or ethylidenenorbornene.
4. Polystyrene and poly(p-methylstyrene).
5. Copolymers of styrene or α-methylstyrene with dienes or acrylic derivatives, such as, for example, styrenebutadiene, styrene-maleic anhydride, styrene-acrylonitrile, styrene-ethyl methacrylate, styrene-butadiene-ethyl acrylate or styrene-acrylonitrile-methacrylate; high impact strength mixtures of styrene copolymers and another polymer, such as, for example, a polyacrylate, a diene polymer or an ethylene-propylene-diene terpolymer; and block copolymers of styrene, such as, for example, styrene-butadiene-styrene, styrene-isoprene-styrene, styrene-ethylene/butylene-styrene or styrene-ethylene/propylene-styrene.
6. Graft copolymers of styrene, such as, for example, styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and mixtures thereof with the copolymers mentioned under 5), which are known, for example, as so-called ABS, MBS, ASA or AES polymers.
7. Polyvinylchloride.
8. Copolymers of vinyl chloride, which can be prepared by the known processes (for example suspension, bulk or emulsion polymerization).
9. Copolymers of vinyl chloride with up to 30% by weight of comonomers, such as, for example, vinyl acetate, vinylidene chloride, vinyl ether, acrylonitrile, acrylic acid esters, maleic acid mono-or diesters or olefins, and graft polymers of vinyl chloride.
10. Halogen-containing polymers, such as, for example, polychloroprene, chlorinated rubber, chlorinated or chlorosulfonated polyethylene and epichlorohydrin homo- and copolymers, in particular polymers of halogen-containing vinyl compounds, such as, for example, polyvinylidene chloride, polyvinyl fluoride and polyrvinylidene fluoride; and copolymers thereof, such as of vinyl chloride-vinylidene chloride, vinyl chloride-vinyl acetate or vinylidene chloride-vinyl acetate.
11. Polymers which are derived from α,β-unsaturated acids and derivatives thereof, such as polyacrylates and polymethacrylates, polyacrylamides and polyacrylonitriles.
12. Copolymers of the monomers mentioned under 11) with one another or with other unsaturated monomers, such as, for example, acrylonitrile-butadiene copolymers, acrylonitrile-alkyl acrylate copolymers, acrylonitrile-alkoxyacrylate copolymers, acrylonitrile-vinyl halide copolymers acrylonitrile-alkyl methacrylate-butadiene copolymers.
13. Polymers which are derived from unsaturated alcohols and amines or their acyl derivatives or acetals, such as polyvinyl alcohol, polyvinyl acetate, stearate, benzoate or maleate, polyvinyl butyral, polyallyl phthalate or polyallylmelamine.
14. Homo-and copolymers of cyclic ethers, such as polyethylene glycols, polyethylene oxide, polypropylene oxide or copolymers thereof with bisglycidyl ethers.
15. Polyacetals, such as polyoxymethylene, and those polyoxymethylenes which contain comonomers, such as, for example, ethylene oxide.
16. Polyphenylene oxides and sulfides and mixtures thereof with styrene polymers.
17. Polyurethanes which are derived from polyethers, polyesters and polybutadienes having terminal hydroxyl groups on the one hand and aliphatic or aromatic polyisocyanates on the other hand, and precursors thereof (polyisocyanate-polyol prepolymers).
18. Polyamides and copolyamides which are derived from diamines and dicarboxylic acids and/or from aminocarboxylic acids or the corresponding lactams, such as polyamide 4, polyamide 6, polyamide 6,6, polyamide 6,10, polyamide 11, polyamide 12, poly-2,4,4-trimethylhexamethyleneterephthalamide, poly-m-phenyleneisophthalamide, and copolymers thereof with polyethers, such as, for example, with polyethylene glycol, polypropylene glycol or polytetramethylene glycol.
19. Polyureas, polyimides and polyamide-imides.
20. Polyesters which are derived from dicarboxylic acids and diols and/or from hydroxycarboxylic acids or the corresponding lactams, such as polyethylene terephthalate, polybutylene terephthalate, poly-1,4 -dimethylol cyclohexane terephthalate, poly-(2,2-bis-(4-hydroxyphenyl)-propane) terephthalate and polyhydroxybenzoates, and block polyether-esters which are derived from polyethylene having hydroxyl end groups, dialcohols and dicarboxylic acids.
21. Polycarbonates and polyester-carbonates.
22. Polysulfones, polyether-sulfones and polyetherketones.
23. Crosslinked polymers which are derived from aldehydes on the one hand and phenols, urea or melamine on the other hand, such as phenol-formaldehyde, urea-formaldehyde and melamine-formaldehyde resins.

24. Drying and non-drying alkyd resins.
25. Unsaturated polyester resins which are derived from copolyesters of saturated and unsaturated dicarboxylic acids with polyhydric alcohols, and vinyl compounds as crosslinking agents, and also their halogen-containing, poorly combustible modifications.
26. Crosslinkable acrylic resins which are derived from substituted acrylic acid esters, such as, for example, epoxy-acrylates, urethane-acrylates or polyesteracrylates.
27. Alkyd resins, polyester resins and acrylate resins which are crosslinked with melamine resins, urea resins, polyisocyanates or epoxy resins.
28. Crosslinkable epoxy resins which are derived from polyepoxides, for example from bis-glycidyl ethers or from cycloaliphatic diepoxides.
29. Naturally occurring polymers, such as cellulose, natural rubber, gelatin and derivatives thereof modified chemically in a polymer-homologous manner, such as cellulose acetates, propionates and butyrates, or cellulose ethers, such as methylcellulose.
30. Mixtures of the abovementioned polymers, such as, for example, PP/EPDM, polyamide 6/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, POM/acrylate, POM/MBS, PPE/HIPS, PPE/polyamide 6.6 and copolymers, PA/HDPE, PA/PP and PA/PPE.
31. Naturally occurring and synthetic organic substances which are pure monomers or mixtures of monomers, such as, for example, mineral oils, animal and vegetable fats, oils and waxes, or oils, fats and waxes based on synthetic esters, or mixtures of these substances.
32. Aqueous dispersions of naturally occurring or synthetic rubber.

The organic polymers to be stabilized can also comprise other additives, for example the following antioxidants:
1. Alkylated monophenols, for example
2,6-di-t-butyl-4-methylphenol,2-t-butyl-4,6-dimethylphenol, 2,6-di-t-butyl-4-ethylphenol, 2,6-di-t-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol or 2,6-di-t-butyl-4-methoxymethylphenol.
2. Alkylated hydroquinones, for example
2,6-di-t-butyl-4-methoxyphenol, 2,5-di-t-butyl-hydroquinone, 2,5-di-t-amyl-hydroquinone or 2,6-diphenyl-4-octadecyloxyphenol.
3. Hydroxylated thiodiphenyl ethers, for example 2,2'-thio-bis-(6-t-butyl-4-methylphenol), 2,2'-thio-bis(4-octylphenol), 4,4'-thio-bis-(6-t-butyl-3-methylphenol) or 4,4'-thio-bis-(6-t-butyl-2-methylphenol).
4. Alkylidene bisphenols, for example
2,2'-methylene-bis-(6-t-butyl-4-methylphenol), 2,2'-methylene-bis(6-t-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-t-butylphenol), 2,2'-ethylidene-bis-(4,6-di-t-butylphenol), 2,2'-ethylidene-bis-(6-t-butyl-4-isobutylphenol), 2,2'-methylene-bis-[6-(α-methylbenzyl)-4-nonylphenol]2,2'-methylene-bis-[6-α, α-dimethylbenzyl)-4-nonylphenol], 4,4'-methylene-bis-(2,6-di-t-butylphenol), 4,4'-methylene-his (6-t-butyl-2-methylphenol), 1,1-bis-(5-t-butyl-4-hydroxy-2-methylphenyl)-butane, 2,6-di-(3-t-butyl-5-methyl-2-hydroxybenzyl)-4-methylphenol, 1,1,3-tris-(5-t-butyl-4-hydroxy-2-methylphenyl)-butane, 1,1-bis-(5-t-butyl-4-hydroxy-2-methylphenyl)-3-n-dodecylmercaptobutane, di-(3-t-butyl-4-hydroxy-5-methylphenyl)-dicyclo-pentadiene, di-[2-(3'-t-butyl-2'-hydroxy-5'-methyl-benzyl)-6-t-butyl-4-methyl-phenyl]terephthalate, or ethylene glycol bis-[3,3-bis-(3'-t-butyl-4'-hydroxyphenyl)-butyrate].
5. Benzyl compounds, for example
1,3,5-tri-(3,5-di-t-butyl-4-hydroxybenzyl)-2,4,6-trimethyl-benzene, di-(3,5-di-t-butyl-4-hydroxybenyl) sulfide, isooctyl 3,5-di-t-butyl-4-hydroxybenzyl-mercaptoacetate, bis-(4-t-butyl-3-hydroxy-2,6-dimethylbenzyl) dithiolterephthalate, 1,3,5-tris-(3,5-di-t-butyl-4-hydroxybenzyl) isocyanurate, 1,3,5-tris-(4-t-butyl-3-hydroxy-2,6-dimethylbenzyl) isocyanurate, or dodecyl 3,5-di-t-butyl-4-hydroxybenzylphosphonate or the calcium salt of 3,5-di-t-butyl-4-hydroxybenzyl phosphonic acid monoethyl ester.
6. Acylamino phenols, for example
4-hydroxy-lauranilide, 4-hydroxy-stear-anilide, 2,4-bis-octylmercapto-6-(3,5-di-t-butyl-4-hydroxy-anilino)-s-triazine or octyl N-(3,5-di-t-butyl-4-hydroxyphenyl)carbamate.
7. Esters of β-(3,5-di-t-butyl-4-hydroxyphenyl)-propionic acid with mono- or polyhdric alcohols, such as, for example, with
methanol, diethylene glycol, octadecanol, triethylene glycol, 1,6-hexanediol, pentaerythritol, neopentylglycol, tris-hydroxyethyl isocyanurate, thiodiethylene glycol or di-hydroxyethyl-oxalamide.
8. Esters of β-(5-t-butyl-4-hydroxy-3-methylphenyl)propionic acid with mono-or polyhydric alcohols, such as, for example, with
methanol, diethylene glycol, octadecanol, triethylene glycol, 1,6-hexanediol, pentaerythritol, neopentylglycol, tris-hydroxyethyl isocyanurate, thiodiethylene glycol or di-hydroxyethyl-oxalamide.
9. Amides of β-(3,5-di-t-butyl-4-hydroxyphenyl)-propionic acid, such as, for example,
N,N'-di-(3,5-di-t-butyl-4-hydroxyphenylpropionyl)-hexamethylenediamine, N,N'-di-(3,5-di-t-butyl-4-hydroxyphenylpropionyl-)trimethylenediamine or N,N'-di-(3,5-di-t-butyl-4-hydroxyphenylpropionyl)-hydrazine.

In addition, the polymers to be stabilized can also comprise other additives, such as, for example:
1. UV absorbers and light stabilizers.
1.1 2-(2'-hydroxyphenyl)-benzotriazoles, such as, for example, the 5'-methyl, 3',5'-di-t-butyl, 5'-t-butyl, 5'(1,1,3, 3-tetramethylbutyl), 5-chloro-3',5'-di-t-butyl, 5-chloro-3'-t-butyl-5'-methyl, 3'-sec.-butyl-5'-t-butyl, 4'-octoxy, 3',5'-di-t-amyl or 3',5'-bis(α,α-dimethylbenzyl) derivatives.
1.2 2-Hydroxybenzophenones, for example the 4-hydroxy, 4-methoxy, 4-octoxy, 4-decyloxy, 4-dodecyloxy, 4-benzyloxy, 4,2', 4'-trihydroxy or 2'-hydroxy-4,4'-dimethoxy derivatives.
1.3 Esters of optionally substituted benzoic acids, for example
4-t-butyl-phenyl salicylate, phenyl salicylate, octylphenyl salicylate, dibenzoylresorcinol, bis-(4-t-butylbenzoyl)resorcinol, benzoylresorcinol, 2,4-di-t-butylphenyl 3,5-di-t-butyl-4-hydroxybenzoate or hexadecyl 3,5-di-t-butyl-4-hydroxybenzoate.
1.4 Acrylates, for example
ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-9-cyano-vinyl)2-methylindoline.

1.5 Nickel compounds, for example nickel complexes of 2,2'-thio-bis-[4-(1,1,3,3-tetramethylbutyl)-phenol], such as the 1:1 or 1:2 complex, optionally with additional ligands, such as n-butylamine, triethanolamine or N-cyclohexyl-diethanolamine, nickel alkyl dithiocarbamates, nickel salts of 4-hydroxy-3,5-di-t-butyl-benzylphosphonic acid monoalkyl esters, such as of the methyl or ethyl ester, nickel complexes of ketoximes, such as of 2-hydroxy-4-methyl-phenyl undecyl ketoxime, nickel complexes of 1-phenyl-4-lauroyl-5-hydroxy-pyrazole, optionally with additional ligands, or nickel salts of 2-hydroxy-4-alkoxybenzophenones.

1.6 Sterically hindered amines, for example 1.6.1 Bis-(2,2,6,6-tetramethylpiperidyl) sebacate, bis-(1,2,2,6,6-pentamethylpiperidyl) sebacate, bis (2,2,6,6-tetramethylpiperidyl) glutarate, bis-(1,2,2,6,6-pentamethylpiperidyl) glutarate, bis-(2,2,6,6 -tetramethylpiperidyl) succinate, bis-(1,2,2,6,6-pentamethyl-piperidyl) succinate, 4-stearyloxy-2,2,6,6-tetramethyl -piperidine, 4-stearyloxy-1,2,2,6,6-pentamethylpiperidine, 4-stearoyloxy-2,2,6,6-tetramethylpiperidine, 4-stearoyloxy-1,2,2,6,6-pentamethylpiperidine, 2,2,6,6-tetramethylpiperidylbehenate, 1,2,2,6,6-pentamethylpiperidylbehenate, 2,2,4,4-tetramethyl-7-oxa-3,20-diazadispiro-[5.1.11.2]-heneicosan-21-one, 2,2,3,4,4-penta-methyl-7-oxa-3,20-diazadispiro-[5.1.11.2]-heneicosan-21-one, 2,2,4,4-tetramethyl-3-acetyl-7-oxy-3,20-diaza-dispiro[5.1.11.2]-heneicosan-21-one, 2,2,4,4-tetramethyl-7-oxa-3,20-diaza-20-(β-lauryloxy-carbonylethyl)-21-oxo-dispiro [5.1.11.2]-heneicosane, 2,2,3,4,4-pentamethyl-7-oxa-3,20-diaza-20-(β-lauryloxy-carbonylethyl)-21-oxo-dispiro [5.1.11.2]-heneicosane, 2,2,4,4-tetramethyl-3-acetyl-7-oxa-3,20-diazo-20-(β-lauryloxycarbonyl-ethyl)-21-oxo-dispiro-[5.1.11.2]-heneicosane, 1,1',3,3',5,5'-hexahydro-2,2',4,4',6,6'-hexaaza-2,2',6,6'-bimethano-7,8-dioxo-4,4'-bis-(1,2,2,6,6-pentamethyl-4-piperidyl)biphenyl, N,N',N'',N''''-tetrakis[2,4]-bis-[N-(2,2,6,6-tetramethyl-4-piperidyl)-butylamino]-1,3,5-triazin-6-yl]-4,7-diazadecane-1,10 -diamine, N,N',N''N''''-tetrakis[2,4-bis -[N(1,2,2,6,6-pentamethyl-4-piperidyl)-butylamino]-1,3,5-triazin-6-yl]-diazadecane-1,10-diamine, N,N',N'',N'''-tetrakis-[2,4-bis-[N-(2,2,6,6-tetramethyl -4-piperidyl)-methoxypropylamino]-1,3,5-triazin-6-yl]-4,7-diazadecane-1,10-diamine, N,N',N'',N''''-tetrakis-[2,4-bis-[N-(1,2,2,6,6-pentamethyl-4-piperidyl)methoxypropylamino]-1,3,5-triazin-6-yl]-2,7-diazadecane-1,10-diamine, bis-(1,2,2,6,6-pentamethyl)-piperidyl)n-butyl-3,5-di-t-butyl-4-hydroxy -benzylmalonate, tris-(2,2,6,6-tetramethyl-4-piperidyl)nitrilotriacetate, tetrakis-(2,2,6,6-tetramethyl-4-piperidyl) 1,2,3,4-butanetetracarboxylate or 1,1'-(1,2-ethanediyl)-bis(3,3,5,5-tetramethyl-piperazinone). 1.6.2 Poly-N,N'-bis(2,2,6,6-tetramethyl-4-piperidyl)-1,8-diazadecylene, the condensation product of 1-(2-hydroxyethyl)-2,2,6,6-tetramethyl-4-hydroxy-piperidine and succinic acid, the condensation product of N,N'-bis(2,2,6,6-tetramethyl-4-piperidyl)-hexamethylenediamine and 4-t-octylamino-2,6-dichloro-1,3,5-triazine or the condensation product of N,N'-bis-(2,2,6,6-tetramethyl-4-piperidyl)-hexamethylenediamine and 4-morpholino-2,6-dichloro-1,3,5-triazine.

1.7 Oxalic acid diamides, for example 4,4'-di-octyloxy-oxanilide, 2,2'-di-octyloxy-5,5'-di-t-butyloxanilide, 2,2'-didodecyloxy-5,5'-di-t-butyloxanilide, 2-ethoxy-2'-ethyl-oxanilide, N,N'-bis-(3-dimethylaminopropyl)-oxalamide, 2-ethoxy-5-t-butyl-2'-ethyloxanilide and a mixture thereof with 2-ethoxy-2'-ethyl-5,4-di-t-butyl-oxanilide, or mixtures of o-and p-methoxy-and of o-and p-ethoxy-disubstituted oxanilides.

2. Metal deactivators, for example

N,N'-diphenyloxalamide, N-salicylyl-N'-salicyloylhydrazine, N,N'-bis-salicyloyl-hydrazine, N,N'-bis(3,5-di-t-butyl-4-hydroxyphenylpropionyl)-hydrazine, 3-salicyloylamino-1,2,3-triazole or bis-benzylidene-oxalic acid dihydrazide.

3. Phosphites and phosphonites, for example triphenyl phosphite, diphenyl alkyl phosphite, phenyl dialkyl phosphite, trisnonylphenyl phosphite, trilauryl phosphite, trioctadecyl phosphite, distearylpentaerythrityl diphosphite, tris-(2,4-di-t-butylphenyl) phosphite, diisodecyl-pentaerythrityl diphosphite, bis(2,4-di-t-butylphenyl)-pentaerythrityl diphosphite, tristearyl sorbityl triphosphite, tetrakis-(2,4-di-tbutylphenyl) 4,4'-biphenylenediphosphonite, 3,9-bis-(2,4-di-t-butylphenoxy)-2,4,8,10-tetraoxa-3,9-di-phosphaspiro-[5.5]-undecane or tris-(2-t-butyl-4-thio(2'-methenyl-4'-hydroxy-5'-t-butyl)-phenyl-5-methenyl) phenylphosphite.

4. Compounds which destroy peroxide, for example esters of β-thio-dipropionic acid, for example the lauryl, stearyl, myristryl tridecyl ester, mercaptobenzimidazole, the zinc salt of 2-mercaptobenzimidazole, zinc alkyl dithiocarbamates, dioctadecyl sulfide, dioctadecyl disulfide or pentaerythritol tetrakis-(β-dodecylmercapto)-propionate.

5. Basic co-stabilizers, for example melamine, polyvinylpyrrolidone, dicyandiamide, triallyl cyanurate, urea derivatives, hydrazine derivatives, amines, polyamines, polyurethanes, alkali metal and alkaline earth metal salts of higher fatty acids or phenolates, for example Ca stearate, Zn stearate, Mg stearate, Na ricinoleate, K palmitate, antimony pyrocatecholate or tin pyrocatecholate, or hydroxides and oxides of alkaline earth metals or of aluminum, for example CaO, MgO or ZnO.

6. Nucleating agents, for example 4-t-butylbenzoic acid, adipic acid, diphenylacetic acid or dibenzylidenesorbitol.

7. Fillers and reinforcing agents, for example calcium carbonate, silicates, glass fibers, asbestos, talc, kaolin, mica, barium sulfate, metal oxides and hydroxides, carbon black or graphite.

8. Other additives, for example plasticizers, lubricants, emulsifiers, pigments, optical brighteners, flameproofing agents, antistatics or blowing agents.

The various additional additives of the abovementioned groups 1 to 6 are added to the polymers to be stabilized in an amount of 0.01 to 10, preferably 0.01 to 5% by weight, based on the total weight of the molding composition. The amount of additives of groups 7 and 8 is 1 to 80, preferably 10 to 50% by weight, based on the total molding composition.

The additives are incorporated into the organic polymers by generally customary methods. The incorporation can be carried out, for example, by a procedure in which the compounds, and if appropriate other additives, are mixed into or applied to the polymers immediately after the polymerization or in the melt before or during shaping. The incorporation can also be carried out by applying the dissolved or dispersed compounds to the polymer directly or mixing them into a solution, suspension or emulsion of the polymer, the solvent subsequently being allowed to evaporate, if appropriate. The compounds are also active if they are subsequently introduced into an already granulated polymer in a separate processing step.

The compounds prepared according to the invention can also be added to the polymers to be stabilized in the form of a masterbatch which comprises these compounds, for example, in a concentration of 1 to 75, preferably 2.5 to 30% by weight.

The process according to the invention offers the advantage that by using a solvent mixture and dispensing with a phase transfer catalyst, higher degrees of conversion and therefore a higher product quality are achieved for the same yield. Surprisingly, under the strongly alkaline conditions no reaction of epichlorohydrin with the alcohol contained in the solvent mixture, as would be expected per se, is observed. In all cases, the alcohol employed could be recovered completely.

The following examples and comparison examples serve to illustrate the subject matter of the invention.

EXAMPLE 1 to 6

2,2,4,4-Tetramethyl-7-oxa-3,20-diaza-20-(2,3-epoxypropyl)-21-oxo-dispiro-[5,1,11,2]-heneicosane and the oligomer obtained therefrom.

100.0 g (0.25 mol) of 2,2,4,4-tetramethyl-7-oxa-3,20-diaza-21-oxo-dispiro-[5,1,11,2]-heneicosane hydrochloride as well as 69.4 g (0.75 mol) of epichlorohydrin and 72.8 g of 50% strength aqueous sodium hydroxide solution (0.91 mol of NaOH) were added in succession to 180 g of a mixture of xylene and isopropanol in the ratio shown in Table 1. This mixture was stirred at 80° C. for 30 minutes. The batch was concentrated in vacuo until all the isopropanol and epichlorohydrin were distilled off. The distillate can be used for further batches. 110 g of xylene and 110 g of water were added to the reaction mixture and the phases were separated. The organic phase was washed twice more with 70 g of water each time. After the solvent had been distilled off in vacuo, a colorless oil was obtained, which was the epoxy compound referred to in the heading. This was polymerized in vacuo for three hours at 200° C. A brittle, colorless resin, the yield and solution viscosity of which are also summarized in Table 1, was obtained.

TABLE 1

| Example | Xylene/Iso[1] | Yield [%] | Viscosity[2] [mm²/s] |
|---|---|---|---|
| 1 | 8/1 | 97.0 | 1.69 |
| 2 | 7/2 | 96.3 | 1.81 |
| 3 | 2/1 | 97.0 | 1.97 |
| 4 | 5/4 | 97.2 | 2.04 |
| 5 | 1/2 | 97.8 | 2.12 |
| 6 | 0/1 | 98.1 | 2.01 |

[1]Isopropanol
[2]20% strength solution in toluene at 25° C. in accordance with DGF-M-III 8(75)

Comparison Examples A and B 2,2,4,4-Tetramethyl-7-oxa-3,20-diaza-20-(2,3-epoxypropyl)-21-oxo-dispiro-[5,1,11,2]-heneicosane and the oligomer obtained therefrom.

100.0 g (0.25 mol) of 2,2,4,4-tetramethyl-7-oxa-3,20-diaza-21-oxo-dispiro-[5,1,11,2]-heneicosane hydrochloride, 1.3 g of polyethylene glycol 200 (comparison example A) or 10 drops of tricaprylammonium chloride (comparison example B) as a phase transfer catalyst as well as 69.4 g (0.75 mol) of epichlorohydrin and 72.8 g of 50% strength aqueous sodium hydroxide solution (0.91 mol of NaOH) were added in succession to 180 g of xylene. This mixture was stirred at 80° C. for 30 minutes. After the excess epichlohydrin had been distilled off, 110 g of xylene and 110 g of water were added to the reaction mixture and the phases were separated. The organic phase was washed twice more with 70 g of water each time. After the solvent had been distilled off in vacuo, a colorless oil was obtained, which was the epoxy compound referred to in the heading. This was polymermized in vacuo for three hours at 200° C. A brittle, colorless resin, the yield and solution viscosity of which are summarized in Table 2, was obtained.

TABLE 2

| Comparison Example | Yield [%] | Viscosity[1] [mm²/sec] |
|---|---|---|
| A | 95.6 | 1.75 |
| B | 97.2 | 1.77 |

[1]20% strength solution in toluene at 25° C. according to DGF-M-III 8(75)

The examples show that the phase transfer catalyst which has an adverse effect on the waste water and therefore the environment and is regarded as necessary according to the prior art can advantageously be dispensed with. This is achieved by using a reusable solvent mixture. Surprisingly, the reaction of the starting materials proceeds more completely than when a phase transfer catalyst is used. Higher degrees of polymerization—detectable from the higher solution viscosity of the polymerization products—are obtained under the same polymerization conditions. From the literature, it would have been expected that phase transfer catalysts would be more advantageous in multiphase reactions as in the present case.

We claim:

1. A process for the preparation of a polyalkyl-1-oxa-diazaspirodecane compound of the Formula I

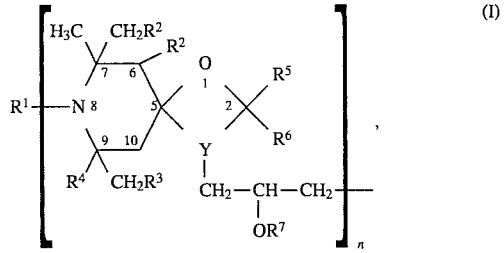

(I)

in which n is an integer from 1 to 50 and

Y is a group of the formula II or III

(II)

(III)

in which the indices 3 and 4 indicate the ring positions in the diazaspirodecane system and one bond of the nitrogen is linked to a $CH_2$ group of the propylene-2-oxy group, $R^1$ is a hydrogen atom, an oxygen atom, an NO group, a $C_1$–$C_{12}$-alkyl group, an allyl group, a $C_1$–$C_{22}$-acyl group, a benzyl group, a $C_1$–$C_{12}$-alkyloxy group or a $C_3$–$C_{12}$-cycloalkoxy group, $R^2$ and $R^3$ are either identical or different and are a hydrogen atom or a $C_1$–$C_5$-alkyl, in which case $R^4$ is a methyl group, or $R^2$ is a hydrogen atom or a $C_1$–$C_5$-alkyl group and $R^3$ and $R^4$, together with the carbon atoms joining them, form a $C_5$- or $C_6$-cycloalkyl group or a group of the formula

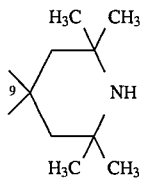

$R^5$ and $R^6$ are identical or different and represent a hydrogen atom, a $C_1$–$C_{30}$-alkyl group or a $C_7$–$C_{12}$-phenylalkyl group which is unsubstituted or substituted by chlorine or $C_1$–$C_4$-alkyl, or $R^5$ and $R^6$, together with the carbon atom joining them, form a $C_5$–$C_{18}$-cycloalkyl group which is unsubstituted or substituted by up to four $C_1$–$C_4$-alkyl groups, or a group of the formula

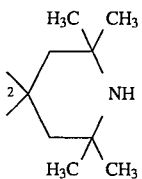

$R^7$, if n=1, has no meaning, so that the oxygen atom is bonded to the terminal $CH_2$ group and forms an oxirane ring, or $R^7$, if n>1 is a hydrogen atom or a $C_1$–$C_{22}$-acyl group, or has no meaning in the terminal monomer unit, so that the oxygen atom is bonded to the terminal $CH_2$ group and forms an oxirane ring, which process comprises reacting a compound of the formula IV

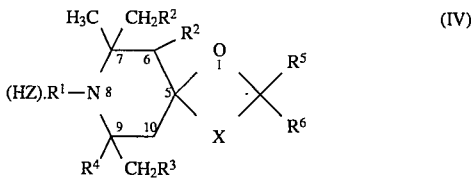

in which $R^1$, $R^2$, $R^3$, $R^4$, $R^5$ and $R^6$ have the above-mentioned meaning, and X is a group of the formula II or formula III in which the indices 3 and 4 indicate the ring positions in the diazospirodecane system and one bond of the nitrogen is linked to a hydrogen atom and HZ is an acid radical, or a salt thereof with a proton acid, with an epihalohydrin of the formula V

in which Hal is a chlorine, bromine or iodine atom, in a molar ratio of 1:1 to 1:10 in the presence of an equimolar to twenty times the molar amount of solid alkali metal hydroxide or of the corresponding amount of solid alkali metal hydroxide in a mixture with water in a weight ratio of 1:9 to 9:1 as the sole catalyst in a solvent mixture of at least one alcohol and if appropriate an inert organic solvent and, if n>1, heating the resulting epoxy compound VI

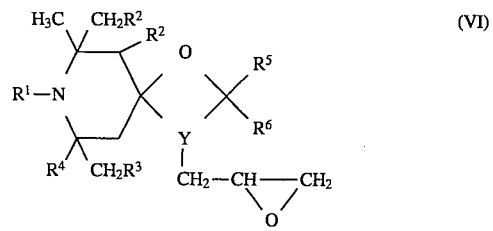

in which $R^1$, $R^2$, $R^3$, $R^4$, $R^5$ and $R^6$ have the above mentioned meaning, to a temperature of 100° to 240° C.

2. The process as claimed in claim 1, wherein the alcohol is a $C_1$ to $C_4$ straight-chain or branched alcohol.

3. The process as claimed in claim 1, wherein 30–70% by weight of the total solvent is alcohol.

4. The process as claimed in claim 1, wherein the alcohol is isopropanol.

5. The process as claimed in claim 1, wherein the inert organic solvent used is toluene or xylene.

6. The process as claimed in claim 1, wherein sodium hydroxide in solid form or mixed with water is used as the catalyst.

7. The process as claimed in claim 1, wherein the compound of the formula IV is 2,2,4,4-tetramethyl-7-oxa-3,20-diaza-21-oxo-dispiro-[5,1,11,2]-heneicosane or its hydrochloride.

8. The process as claimed in claim 1, wherein the compound of the formula V is a epichlorohydrin.

* * * * *